(12) United States Patent
Weinstein

(10) Patent No.: US 6,951,459 B2
(45) Date of Patent: Oct. 4, 2005

(54) METHOD AND APPARATUS FOR COMMUNICATING TOOTH CHARACTERISTICS AND TOOTH RESTORATION PRODUCED THEREBY

(76) Inventor: Steven P. Weinstein, 5141 S. Ironton Way, Englewood, CO (US) 80111

( * ) Notice: Subject to any disclaimer, the term of this patent is extended or adjusted under 35 U.S.C. 154(b) by 207 days.

(21) Appl. No.: 10/156,968

(22) Filed: May 28, 2002

(65) Prior Publication Data
US 2003/0224318 A1 Dec. 4, 2003

(51) Int. Cl.[7] ............................................. A61C 19/10
(52) U.S. Cl. ..................................................... 433/26
(58) Field of Search ................................ 433/26, 203.1

(56) References Cited

U.S. PATENT DOCUMENTS

| | | | | |
|---|---|---|---|---|
| 1,709,066 A | * | 4/1929 | Field ........................... 433/26 |
| 2,341,153 A | * | 2/1944 | Myerson ..................... 433/26 |
| 3,405,446 A | * | 10/1968 | Wiener ....................... 433/215 |
| 3,964,167 A | * | 6/1976 | Yerkes, Jr. .................. 433/26 |
| 5,273,429 A | * | 12/1993 | Rekow et al. .............. 433/215 |
| 5,639,235 A | * | 6/1997 | Lapointe et al. ............ 433/26 |
| 5,685,712 A | * | 11/1997 | Fischer ........................ 433/26 |
| 5,766,006 A | * | 6/1998 | Murljacic .................... 433/26 |
| 5,800,164 A | | 9/1998 | Pfau ............................ 433/26 |
| 6,328,563 B1 | * | 12/2001 | Hobo .......................... 433/26 |
| 6,499,998 B2 | * | 12/2002 | Kerschbaumer et al. ... 433/26 |

* cited by examiner

Primary Examiner—John J Wilson
(74) Attorney, Agent, or Firm—Heimbecher & Assoc., LLC

(57) ABSTRACT

A method and apparatus for communicating specific idiosyncrasies in tooth appearance to be replicated in the fabrication of tooth restorations, as well as a method for creating reference images of a tooth are disclosed. The apparatus contains images of a tooth, wherein categories of specific features are displayed in the images, and codes are assigned to the images according to variations within the categories. The method of communication utilizes the apparatus by allowing a first user to compare an actual tooth to the images, record the codes for images with features that most closely resemble the actual tooth, and transmit the codes to a second user who may reference the same selected images using the recorded codes. The reference images of a particular type of tooth are created by separating and enhancing specific features in photographs of an actual tooth.

5 Claims, 15 Drawing Sheets

Fig. 3B

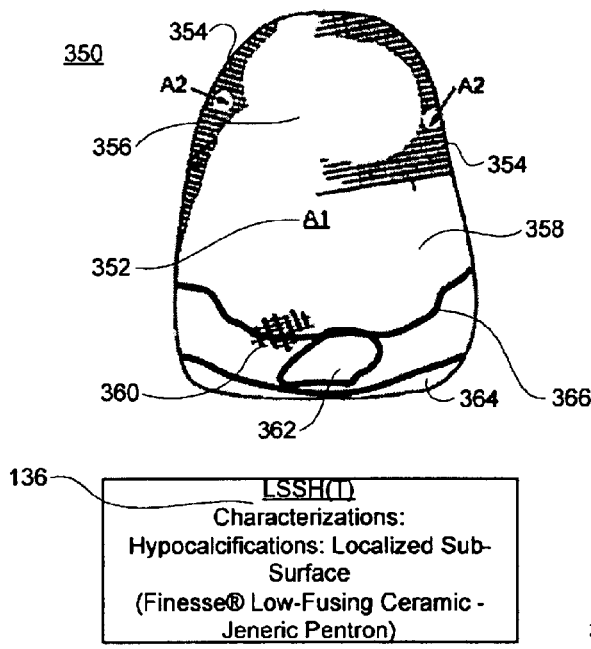

136 — LSSH(T)
Characterizations:
Hypocalcifications: Localized Sub-Surface
(Finesse® Low-Fusing Ceramic - Jeneric Pentron)

Fig. 3C

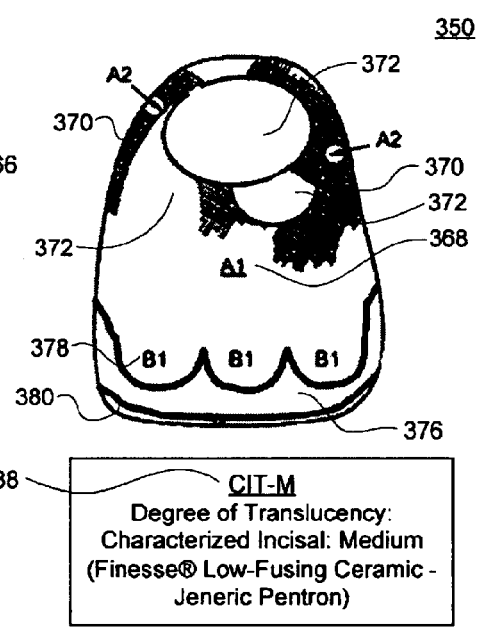

88 — CIT-M
Degree of Translucency:
Characterized Incisal: Medium
(Finesse® Low-Fusing Ceramic - Jeneric Pentron)

Fig. 3D

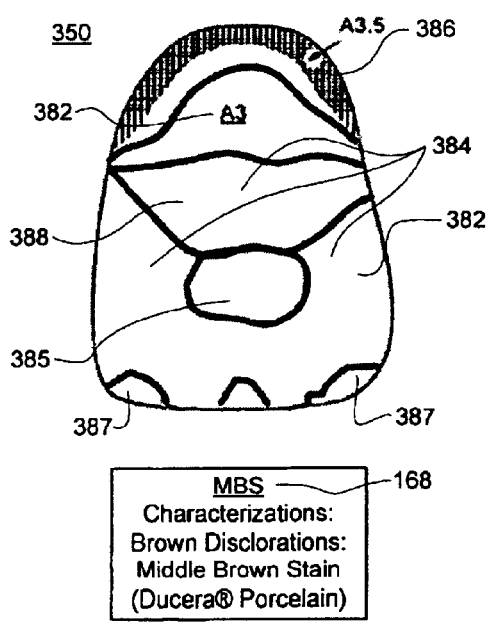

MBS — 168
Characterizations:
Brown Disclorations:
Middle Brown Stain
(Ducera® Porcelain)

Fig. 3E

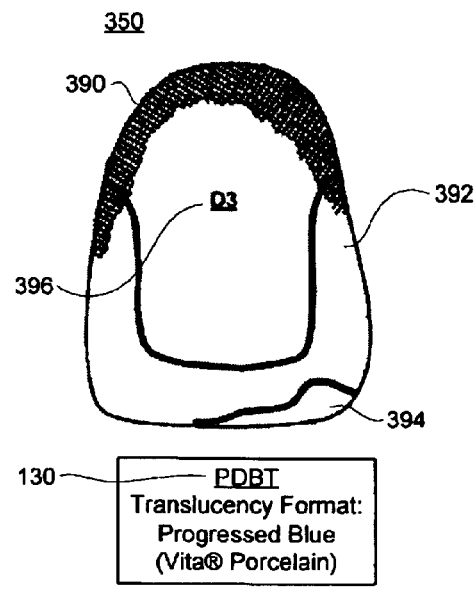

130 — PDBT
Translucency Format:
Progressed Blue
(Vita® Porcelain)

METHOD AND APPARATUS FOR COMMUNICATING TOOTH CHARACTERISTICS AND TOOTH RESTORATION PRODUCED THEREBY

BACKGROUND OF THE INVENTION

1. Field of the Invention

This invention relates to the communication between dentists, dental auxiliaries, and laboratory technicians of specific idiosyncrasies in tooth appearance to be replicated in the fabrication of porcelain or ceramic restorations.

2. Description of Related Art

Traditional methods of assigning features or characterizations in tooth appearance for the purpose of accurate and consistent communication of the appearances from a dentist or dental auxiliary to a laboratory require a significant input of information for a life-like output in a final restoration of a patient's tooth. The dentist who provides greater detail in the nature and intensity of desired tooth characteristics is much more likely to have a positive result than the dentist who provides a less specific description. Likewise, the laboratory technician who is able to reference more detailed information has a much higher potential to achieve a positive result than one who is provided limited information. While traditional methods may sometimes be successful, there are many variables that can complicate the process, resulting in inadequate or misinterpreted communication, which in turn lead to greater time demands for treatment.

Features relevant to tooth appearance can be communicated from the dental office to the dental ceramist through several different means. For instance, the dentist or dental auxiliary may create a diagrammatic illustration depicting various specific features of tooth appearance including narratives. Tooth appearance may be communicated to the dental ceramist using photographic technology, such as a 35 mm color print or a digital photo image transmitted electronically. Alternatively, the ceramist may examine the patient directly while simultaneously creating his or her own schematic or recording tooth appearance using photographic technology for later reference. Prescribing particular features and fabricating restorations to fulfill these requirements is performed on an individual basis requiring one or a combination of the aforementioned methods of communication for each patient.

While current techniques may allow for successful replication of particular features relevant to tooth appearance, significant limitations exist leading to increased time and equipment costs, as well as error that is introduced through the subjectivity of interpretation and multiple steps in communicating the desired results. For instance, the ability to adequately identify and describe features of tooth appearance varies among dentists and dental auxiliaries depending upon motivation, experience, and skills. When using photography, multiple variables are introduced that may compromise dependability, for example, method of display, exposure, subject framing, film processing, and loss of feature contrast or detail due to flash illumination coupled with the fact that certain features are difficult to consistently capture photographically. The use of photography also requires additional expenses in equipment, film, and film processing. The use of photographs, diagrams, and narratives provided to the ceramist are subjectively interpreted and susceptible to error when changing contexts from one case to the next.

Presently there is no industry standardization in the categorization and encoding of features in tooth appearance that allow for accurate descriptions of the degree or intensity of features in tooth appearance. Esthetic dentistry, by its very nature, is a very visual endeavor wherein all parties are trying to translate a visual impression of what they see and what they would like to see in a completed dental restoration into words. There is a need for a process of accurately matching a restoration to natural definition that is less difficult, time consuming, and expensive than traditional methods when considering varying degrees in motivation and abilities of a dentist and a laboratory technician. An improved process would reduce or eliminate the inability to achieve an acceptable and anticipated result and the subsequent need to re-make restorations. An improved process would also reduce patient frustration and treatment time, as well as uncompensated costs to the dentist and technician in time, effort, and materials.

SUMMARY OF THE INVENTION

The present invention addresses the shortcomings of the tooth restoration process by inexpensively creating a level of standardization in the communication of specific idiosyncrasies in tooth appearance to be replicated in the fabrication of porcelain and/or ceramic restorations by significantly reducing the amount of subjectivity associated with such communications. The invention provides a communication tool for reference by the dentist and dental laboratory in order to fabricate life-like restorations. Repetitive use of the invention may also enable the dentist and laboratory to provide consistent and predictable results. Additionally, the present invention significantly reduces the amount of expertise required to facilitate communications between dentists, dental auxiliaries, and ceramists and further facilitates such communications in a more consistent and objective manner.

In one embodiment, the present invention depicts, categorizes, and encodes specific features of tooth appearance in a communication tool to enable documentation of the features. The array of features depicted may be sufficiently inclusive so as to command applicability to tooth characterizations or features with which any patient may present. Categories representing features of tooth appearance are presented with specific illustrations of variation within each category. Illustrations representing variations in degree and intensity of particular features are also provided. Specific features diagnosed are transcribed on an accompanying laboratory prescription and sent to the dental laboratory where the restoration may be fabricated. The laboratory technician or ceramist may refer to the same pictorial display in fabricating the porcelain or ceramic portions of the restoration that have been delineated on the laboratory prescription to accurately create the prescribed presentation of the final restoration.

Basing communication on pictorial images eliminates the need for complex diagrams or narratives, and fixed presentation of the images reduces the negative impact of metamerism (i.e., the change in appearance caused by different lighting conditions). Thus, the error and potential error in current formats and methods of communicating features may be minimized or eliminated. Additionally, the dentist sets all technical parameters and directs the laboratory technician to stay within the parameters in order to support accountability of the technician in following direction of the dentist. The content and format of the images support recognition of individual features because, with repetitive use, the user is trained to recognize these features both singly and in composite. Therefore, the invention is conducive to use by dental auxiliaries who may have less knowledge, training, or experience in the field by improving the communication of these less skilled practitioners.

The images presented in the present invention may be a singularity on an unchanging template. Composite representations of multiple specific features in context may also be presented as a secondary reference. Displaying single features on a constant template eliminates visual distractions inherent with changing contexts. Displaying both single features and composite images provides for immediate reference to verify the accuracy of selected features. In either case, the dimensions of the gingival tissue framing the tooth and the dimensions of the tooth template may remain constant. Representative slides based on clinical observations may be converted to a digital format and specific features may be digitally separated from the original image and applied to the respective template. All features depicted in the present invention thus may be true representations of natural phenomenon. In some cases, further digital manipulation of an image may be used to heighten or enhance the respective feature in order to maintain its natural appearance. The images may be sufficiently large to enable deciphering of detail while not demanding extraordinary perceptual interpolation or extrapolation by the user for accuracy.

When using the present invention while examining a patient in order to select specific features that occur in tooth appearance, a dentist or dental auxiliary may first select a category of feature. The dentist or dental auxiliary will then compare the images displayed for the selected category to the patient's tooth. The dentist or dental auxiliary will then document the code for the image that most closely depicts the actual features on the tooth on a prescription form. If the images are displayed, for example, in a booklet, diagnosed features may be transcribed on a laboratory prescription form that is consistent with the booklet itself. The lab technician or ceramist will then use the codes documented on the prescription form to cross reference to identical images displayed using the present invention in the laboratory in order to fabricate a porcelain and/or ceramic restoration of the patient's tooth.

The invention may also utilize semi-transparent overlays of various images displaying specific selected features of tooth appearance in order to construct a composite image of the tooth. However, when overlaying layers, for example, of acetate, one must be sure that a lifelike image is attainable. In addition to semi-transparent overlays, the invention may utilize a video display to present composite images of the tooth for reference by the dentist or technician, for example, through the use of image morphing software on a computer. When using video displays, care be must be exercised to make sure the consistency of the images is not compromised by such equipment variables as monitor calibration.

These and additional features and advantages of the present invention will become more apparent from a reading of the following detailed description when taken in conjunction with the accompanying drawings.

BRIEF DESCRIPTION OF THE DRAWINGS

This patent or application file contains at least one drawing executed in color. Copies of this patent or patent application publication with color drawings will be provided by the U.S. Patent and Trademark Office upon request and payment of the necessary fee.

DETAILED DESCRIPTION OF EMBODIMENTS OF THE INVENTION

The present invention will now be described in detail with reference to various embodiments thereof, with some aspects of the invention being described in the accompanying drawings. Numerous specific details are set forth in order to provide a thorough understanding of the present invention. It will be apparent to those skilled in the art that the present invention may be practiced without some or all of the specific details, that operations may be rearranged, that some operations may be eliminated or performed in a different way, and that other changes may be made without departing from the spirit and scope of the present invention.

An exemplary embodiment of the present invention is referred to herein as a Laboratory and Dentist Digitally Enhanced Reference (LADDER). The LADDER is a pictorial reference guide displaying true photographic images of features of tooth appearance. The scope, intensity, coloration, contrast, and character of the features are combined to simplify what would otherwise be a significantly more involved means of communication into one universal pictorial and encoded reference. Dentists, dental auxiliaries, and laboratory technicians may use the LADDER to communicate these features between the dental office and dental laboratory. The LADDER depicts, categorizes, and encodes specific features that occur in tooth appearance in the context of an unchanging template, enabling the user to visualize the specific feature(s) and readily communicate such onto a laboratory prescription for fabrication of a porcelain or ceramic restoration. Samples of composite features are also included in the LADDER to provide further reference. The encoded prescription is then forwarded to the laboratory technician or ceramist who references the same images to accurately replicate the prescribed feature(s) in the porcelain or ceramic restoration.

Respective tooth features are accurately depicted in the LADDER on a constant template in both individual and composite formats. The features and images depicted may be digitally reconstructed to be accurate in reflecting a life-like appearance. A constant template is maintained with only the respective tooth feature changing. Specific tooth features are identified using the LADDER and are added individually to create the final appearance. The LADDER allows any user to identify specific features, and [while= during the time that] the respective coding provides for exact communication of the identified features to the laboratory. Once the specific features are identified, the user can utilize the composite images provided in the LADDER to verify and support the accuracy of his or her selection(s) in a literal, photographic context.

Figure 1A:
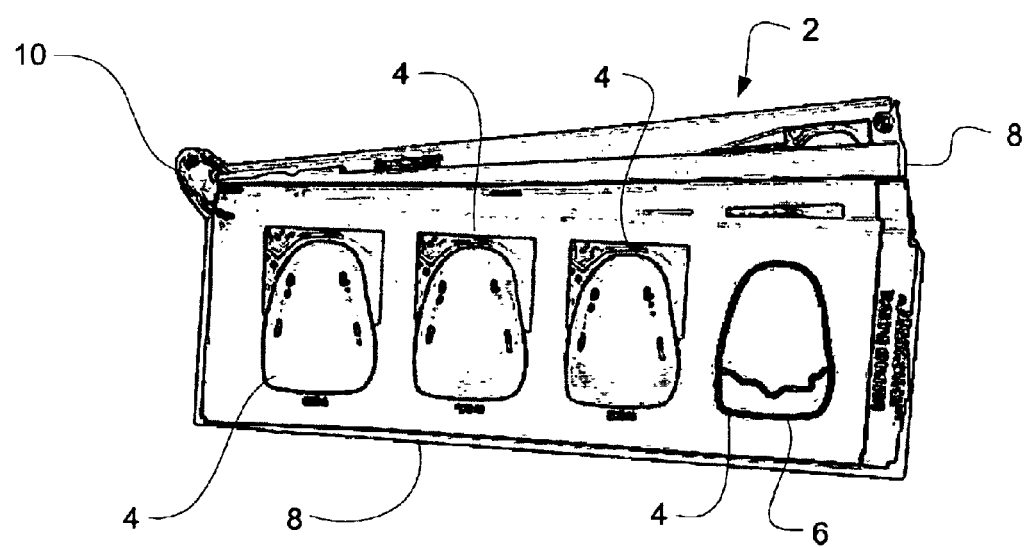
FIGS. 1A and 1B are front isometric views of a communication tool of the present invention in a booklet form.
Figure 1B:
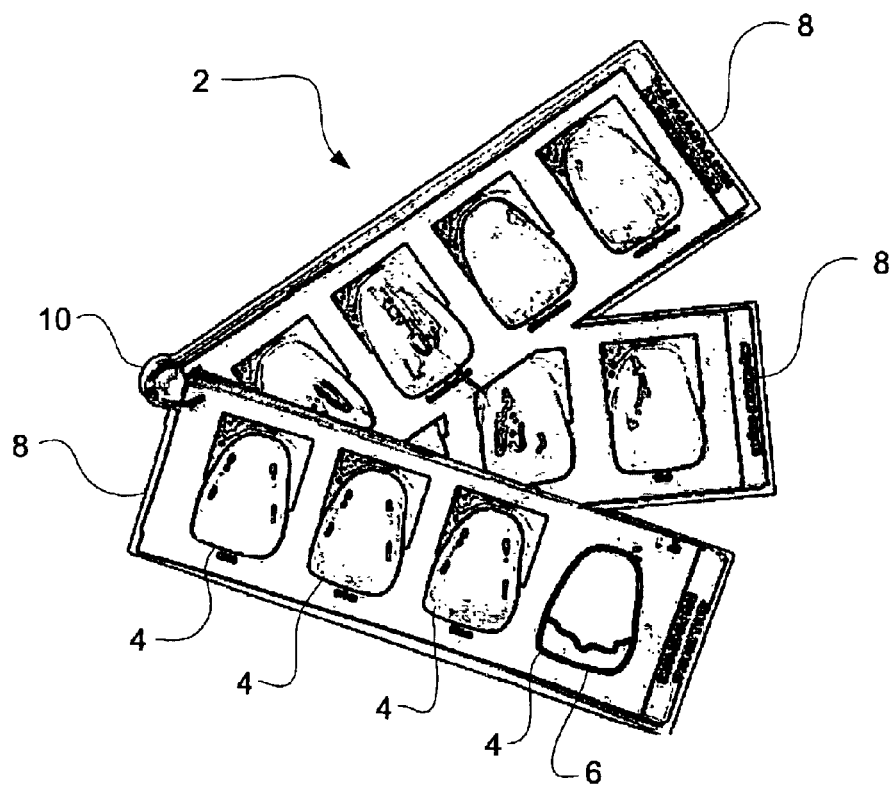

In one embodiment, the LADDER utilizes a multi-page booklet 2, as depicted in FIGS. 1A and 1B, including front and back covers with images 4 and schematics 6 displayed inside. A plurality of images 4 may be displayed on each of the internal pages 8 of the booklet 2. The embodiment depicted in FIGS. 1A and 1B displays four images 4 per page 8. The pages may also be connected together to allow for viewing of a single page with all others rotated under and against the topmost page and for viewing multiple pages by fanning the desired pages. For example, the pages of the booklet may be connected in the upper left hand corner by a binding ring 10, as shown in FIGS. 1A and 1B. The binding ring 10 allows for viewing a single page 8 with all others rotated under and against the topmost page as shown in FIG. 1A and for viewing multiple pages by rotating the pages 8 using the binding ring as a pivot point to fan desired pages as shown in FIG. 1B.

Figure 2:
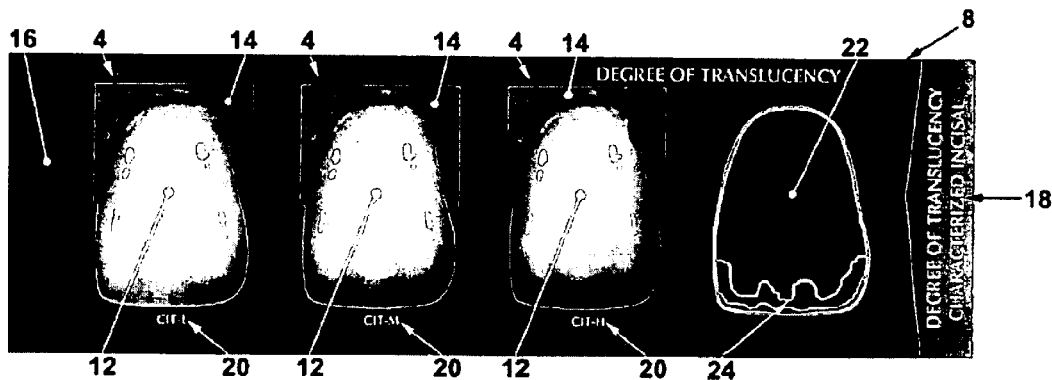
FIG. 2 is a plan view of a single page of a communication tool of the present invention in a booklet form.

FIG. 2 depicts a typical page 8 in one embodiment of the LADDER booklet. The page 8 in FIG. 2 displays three images 4 of an ideal maxillary left central incisor 12, set into a template representing attached gingival tissue 14 that acts to mimic a natural setting. The images are further printed on a matte black background 16 for contrast. More or fewer than four images 4 may be displayed on the page in various ways, and the LADDER booklet is not limited to containing images 4 of ideal maxillary left central incisor 12, but may contain images 4 of any type of tooth. The images 4 may be printed on only one side of the page 8, or both sides may also be utilized. Multiple categories delineating multiple features of tooth appearance may be displayed on the pages of the LADDER booklet. For example, the page 8 depicted in FIG. 2 displays a category name 18 vertically on the right hand side of the page 8 and may also be color coded. The images 4 displayed on a page 8 may represent variations within a specific category. For example, the embodiment shown in FIG. 2 shows images 4 that represent low, medium, and high translucency. The images 4 in FIG. 2 may also have designated codes 20: CIT-, CIT-M, and CIT-H. The page 8 may also display a schematic drawing 22 of the image 4 showing the geographic location 24 on the tooth of the referenced feature. It may be desirable to include the number of images per page that should support presentation of those categories that display the degree or intensity of a particular feature. Presenting multiple and defined images per page may assist the user in discerning features by comparison within a category that otherwise may be difficult to perceive.

When using a booklet to display images, the size may be compact to make it convenient to use chair-side in referencing the natural dentition of a patient, as well as on the work surface of the laboratory technician when fabricating the final restoration. All pages of the booklet may also be laminated so they may be cleaned or disinfected without damaging the booklet. Images may be displayed that are sufficiently large to enable the deciphering of detail while maintaining proportion to the subject reference that does not demand extraordinary perceptual interpolation or extrapolation by the user for accuracy. For example, one embodiment of the invention displays images that are approximately 1.5" high and 1" wide.

When examining a patient to document how a particular tooth restoration should appear, a dentist or dental auxiliary may use the LADDER to effectively communicate the specific features of tooth appearance to the laboratory technician. The specific features of tooth appearance may be transcribed on a prescription form. FIG. 3 shows one embodiment of a prescription form, which is herein referred to as a LADDER Rx form 300. The LADDER Rx form 300 may contain blank spaces for information to be filled in by the dentist or dental auxiliary, such as the dentist's name 302; the dentist's license number 304; the date of the prescription 306; the patient's name 308, the dentifrice material 310, i.e., the brand or type of material to be used in making the tooth restoration, e.g., Vita® porcelain (Vita, Bad Sackingen, Germany); and the desired return date 312. The LADDER Rx form 300 may also contain blank schematic drawings 314 of a tooth, whereby the dentist may indicate the types of specific features and their locations on the patient's tooth, which are explained in further detail herein.

Figure 5:
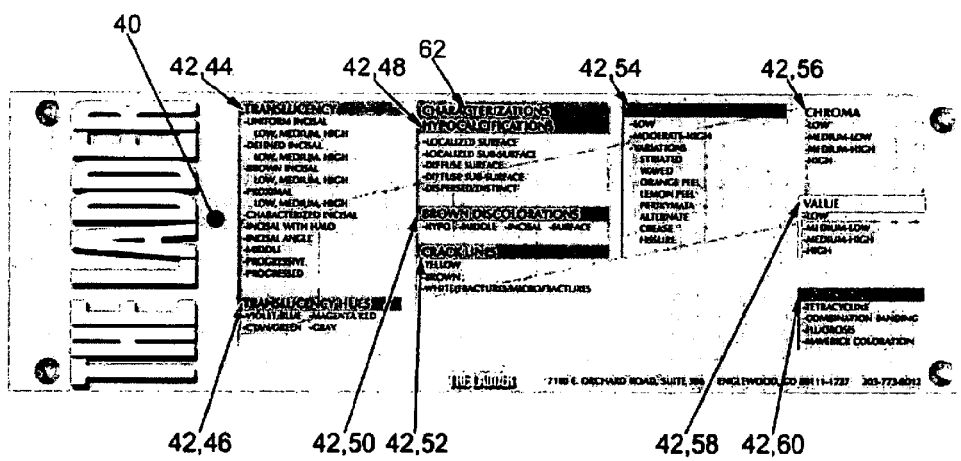
FIG. 5 is a plan view of an index of one embodiment of a communication tool of the present invention in a booklet form.
Figure 4B:
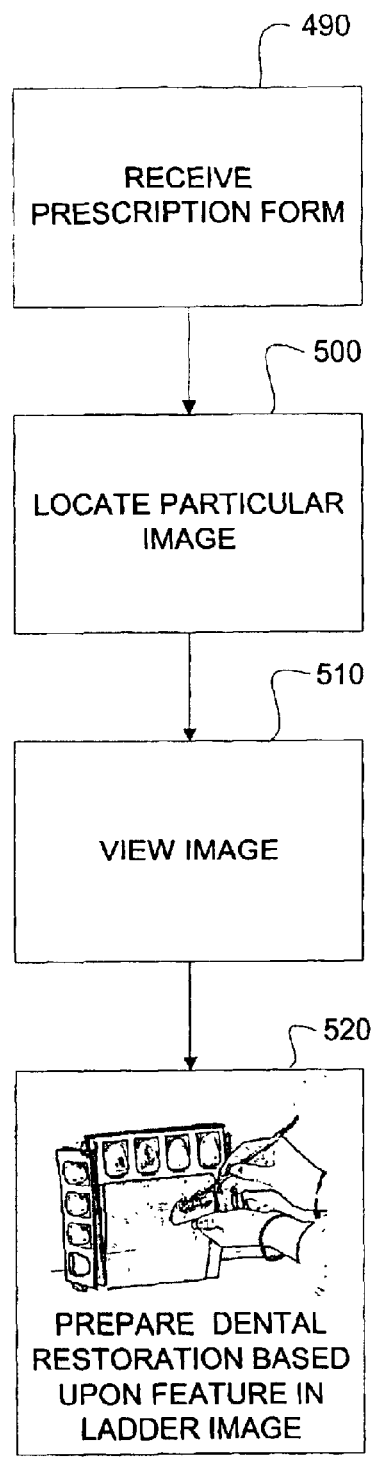
FIGS. 4A and 4B are flow diagrams depicting a method for using a communication tool of the present invention in a booklet form.
Figure 4A:
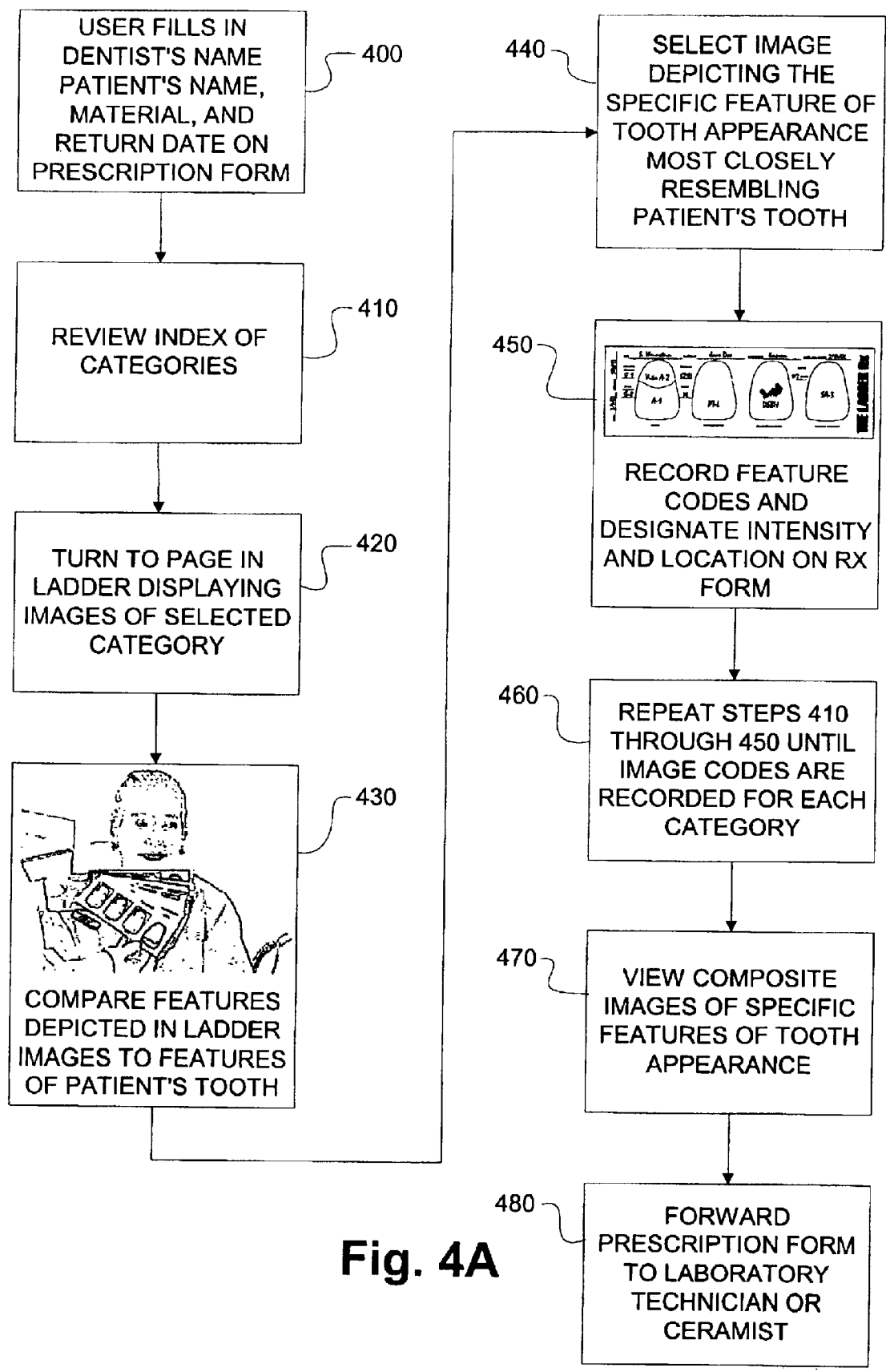

One method for using the LADDER is depicted in FIGS. 4A and 4B. At step 400, the dentist or dental auxiliary fills in the dentist's name, the patient's name, the material from which the restoration will be fabricated (e.g., porcelain to metal (gold), a specific brand of ceramic, or a specific type of feldspathic porcelain), and the return date on the LADDER Rx form. The dentist or dental auxiliary may then, at step 410, choose to review an index of categories of specific features of tooth appearance. An index of categories for one embodiment of a LADDER booklet is depicted in FIG. 5. Then, at step 420, the dentist or dental auxiliary turns to the page, if using a booklet, containing the images of the chosen category. The displayed images for the specific category are then, at step 430, compared to the patient's actual tooth. The dentist or dental auxiliary then selects the image containing the specific feature of tooth appearance within the chosen category that most accurately reflects the patient's actual tooth (step 440). Once an image is selected, the dentist or dental auxiliary then, at step 450, records the code corresponding to the selected image on the prescription form and further indicates the location and intensity of the feature on the actual tooth by marking an area on the schematic drawings of the tooth on the prescription form. Steps 410 though 450 are then repeated until image codes have been selected and documented for each category (step 460). Once all the image codes have been recorded, the dentist or dental auxiliaries may then, at step 470, view composite images of specific features of tooth appearance in order to verify their code selections. At step 480, the prescription form is forwarded to the laboratory technician or ceramist in charge of creating the tooth restoration.

Referring to FIG. 4B, the laboratory technician or ceramist receives the completed prescription form at step 490. While viewing a LADDER reference guide that is duplicate to the one used by the dentist or dental auxiliary, the laboratory technician or ceramist, at step 500, uses the prescription form to guide him or her to specific images during fabrication of the tooth restoration. At step 5 10, the laboratory technician or ceramist views the image to better understand the desired tooth restoration. Finally, at step 520, the laboratory technician or ceramist places the image so that it may be viewed while preparing the tooth restoration and prepares the tooth restoration based upon the features displayed in the image.

FIGS. 5–15 depict one exemplary embodiment of a LADDER booklet. FIG. 5 depicts an index 40 for this embodiment of the LADDER booklet. The index 40 shows nine categories 42 depicting multiple features of tooth appearance. The categories 42 depicted in FIG. 5 are translucency 44, translucency hues 46, hypocalcifications 48, brown discolorations 50, crack lines 52, surface anatomy 54, chroma 56, value 58, and variations 60. The hypocalcifications 48, brown discolorations 50, and crack lines 52 categories may be grouped under a heading of characterizations 62. The categories 42 displayed on the index 40 may also be color coded to identify images of like categories 42 for ease of locating a specific category 42 when using the LADDER. For example, translucency 44 and translucency hues 46 may be displayed in blue; hypocalcifications 48, brown discolorations 50, and crack lines 52 may be displayed in gray; surface anatomy 54 may be displayed in red; chroma 56 may be displayed in yellow; value 58 may be displayed in white; and variations 60 may be displayed in violet. The respective color coding 63 of the categories may also be present as a background for narrative descriptions vertically transcribed on the right-hand side of each page, as shown, for example, in FIG. 6A. The embodiment of the LADDER described herein is presented for use with a maxillary left incisor. However, the LADDER may be used with any tooth, and the categories discussed could vary in number, name, and detail.

Figure 6A:
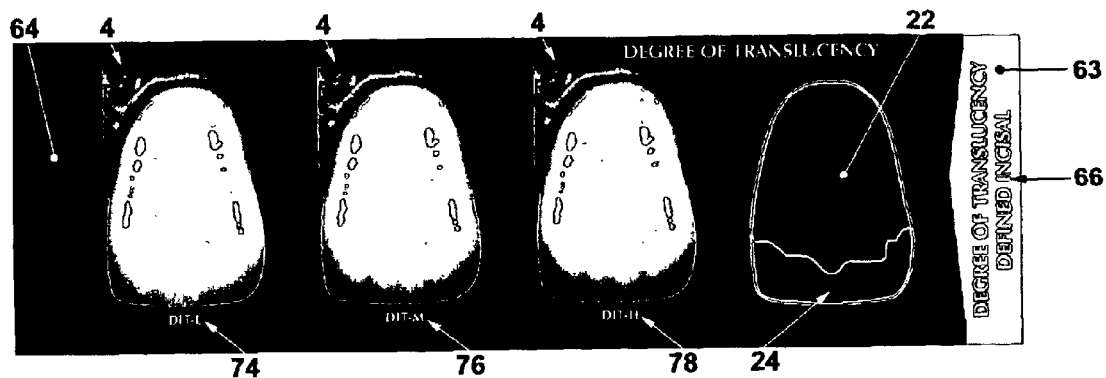
FIG. 6A is a plan view of a Defined Translucency page of the booklet of FIG. 5.
Figure 6B:
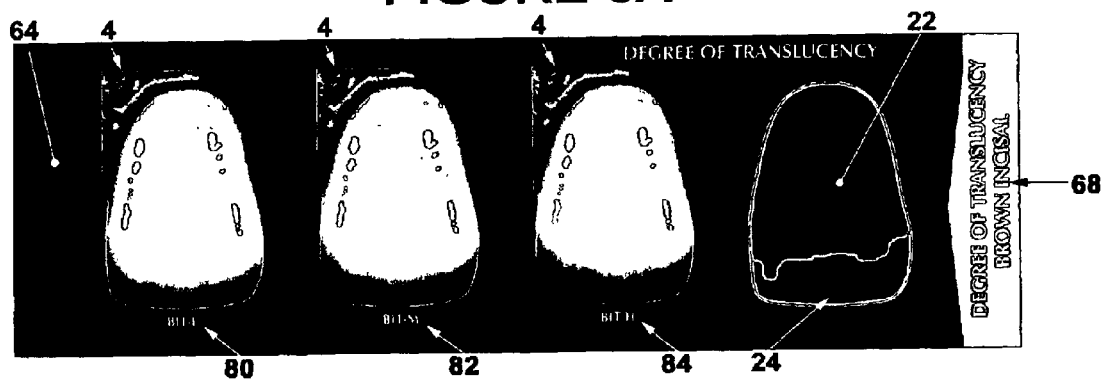
FIG. 6B is a plan view of a Brown Translucency page of the booklet of FIG. 5.
Figure 6C:
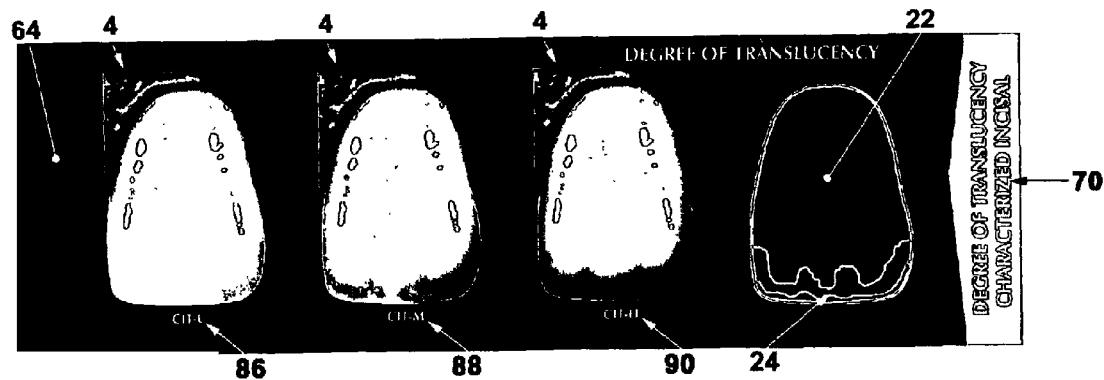
FIG. 6C is a plan view of a Characterized Translucency page of the booklet of FIG. 5.
Figure 6D:
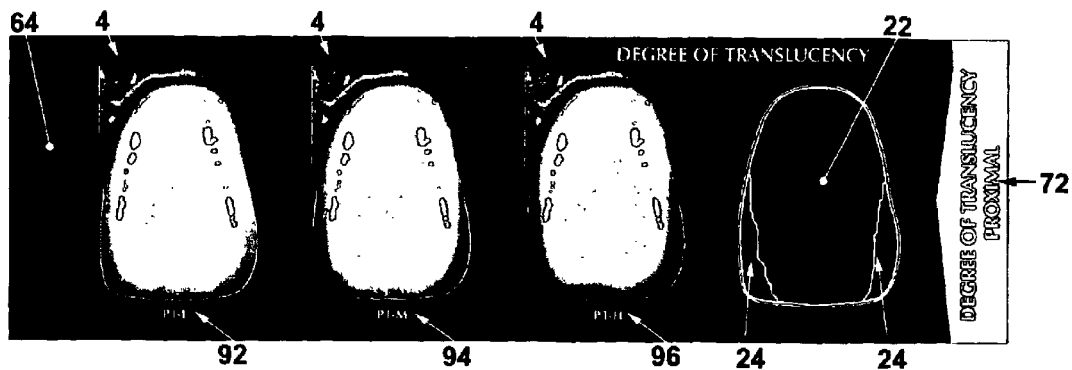
FIG. 6D is a plan view of a Proximal Translucency page of the booklet of FIG. 5.

Four translucency pages 64 (FIGS. 6A–6D) are presented in the LADDER booklet: defined 66 (FIG. 6A); brown 68 (FIG. 6B); characterized 70 (FIG. 6C); and proximal 72 (FIG. 6D). In the embodiment depicted, each translucency page 64 displays three images 4 depicting a low, moderate, and high degree of translucency. A schematic drawing 22 of the image 4 showing the geographic location 24 of the referenced feature may also be shown on each of the translucency pages 64. Each image 4 is coded for the type and degree of translucency. In FIG. 6A, the defined images 4 may be coded as follows: DIT-L 74 for defined incisal low, DIT-M 76 for defined incisal medium, and DIT-H 78 for defined incisal high. As shown in FIG. 6A, the tooth in each image becomes more translucent toward the bottom of the tooth from DIT-L to DIT-H. In FIG. 6B, the brown images 68 may be coded as follows: BIT-L 80 for brown incisal low, BIT-M 82 for brown incisal medium, and BIT-H 84 for brown incisal high. As shown in FIG. 6B, the tooth in each image becomes darker brown toward the bottom of the tooth from BIT-L to BIT-H. In FIG. 6C, the characterized images 70 may be coded as follows: CIT-L 86 for characterized incisal low, CIT-M 88 for characterized incisal medium, and CIT-H 90 for characterized incisal high. These images differ from the defined translucency series of FIG. 6A in that the translucent area does not extend to the bottom edge of the tooth. As shown in FIG. 6C, the translucent area of the tooth in each image becomes more translucent toward the bottom and the sides closer to the bottom of the tooth from CIT-L to CIT-H. In FIG. 6D, the proximal images 72 may be coded as follows: PT-L 92 for proximal translucency low, PT-M 94 for proximal translucency medium, and PT-H 96 for proximal translucency high. As shown in FIG. 6D, the tooth in each image becomes more translucent at both sides of the tooth from PT-L to PT-H.

Figure 7:
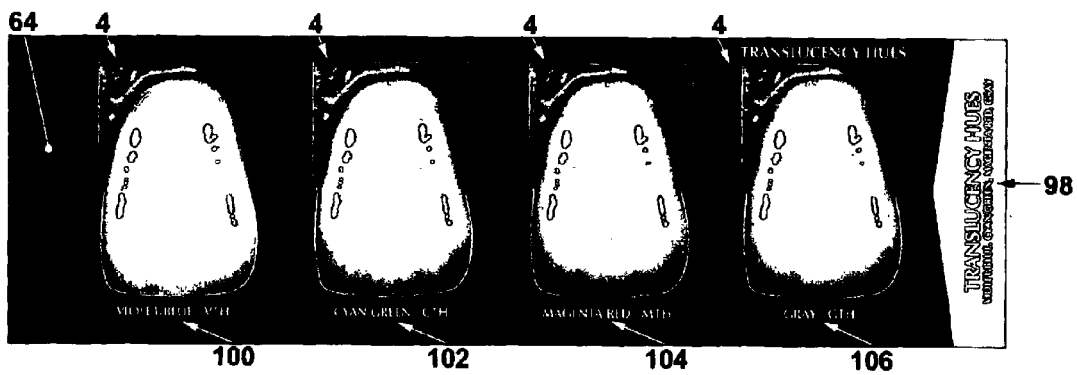
FIG. 7 is a plan view of a Translucency Hues page of the booklet of FIG. 5.

Translucency hues 46 (FIG. 5) is a sub-category of translucency 44 and is described on a separate page 98 (FIG. 7), utilizing four images 4. All aspects of the images 4 are constant except for the hue or color of the referenced translucency. As shown in FIG. 7, the tooth images are more translucent toward the bottom of the tooth, and the translucency varies by color. In FIG. 7, each image 4 is coded with as follows to describe the varying colors of translucency on each image: VTH 100 for violet blue translucency hue, CTH 102 for cyan/green translucency hue, MTH 104 for magenta/red translucency hue, and GTH 106 for gray translucency hue.

Figure 8A:
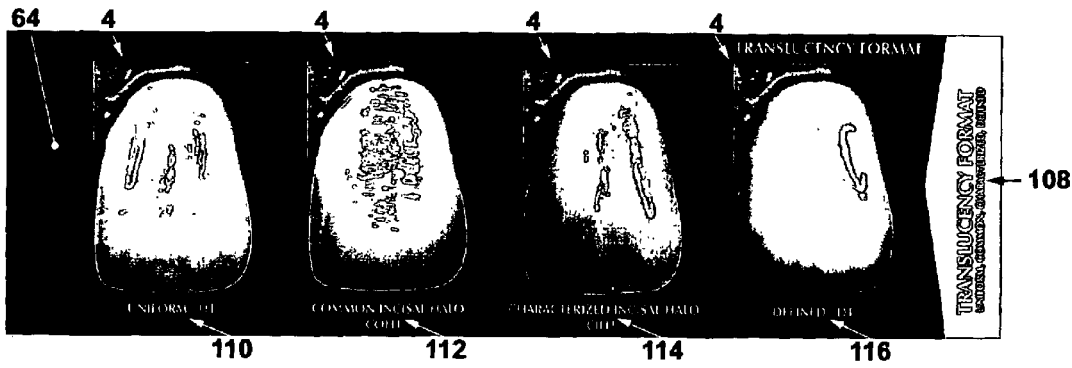
FIGS. 8A–8C are plan views of Translucency Format pages of the booklet of FIG. 5.
Figure 8B:
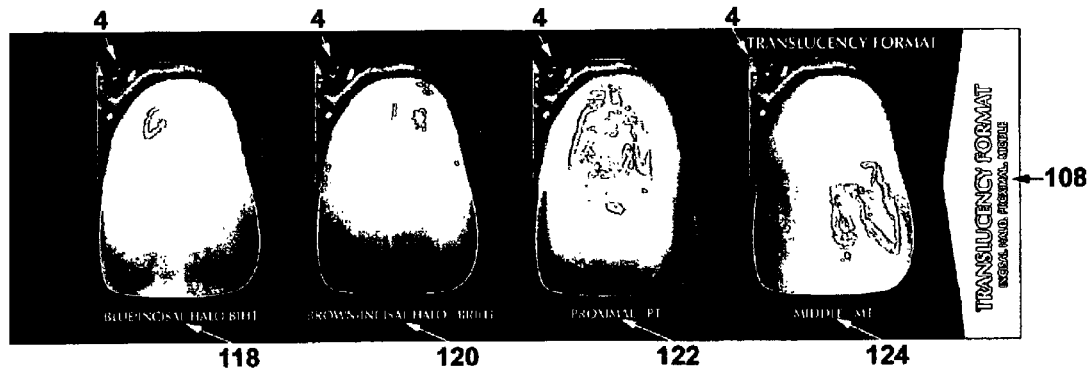
Figure 8C:
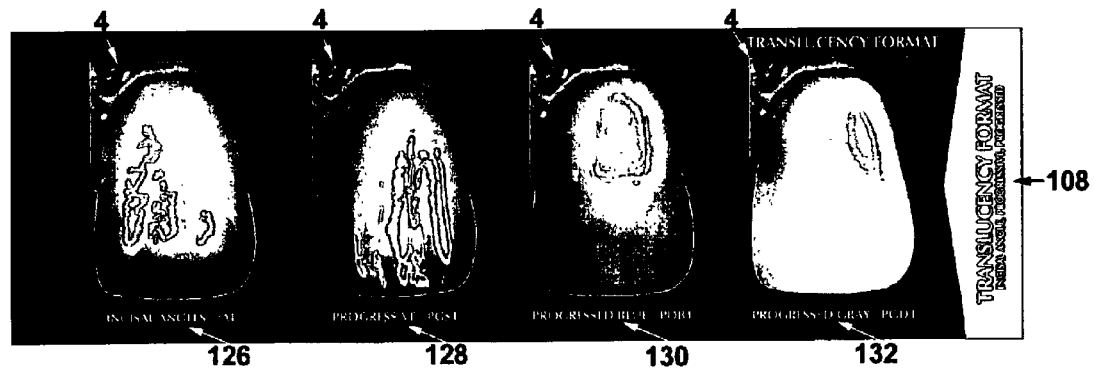

Referring to FIGS. 8A–8C, the twelve images displayed on the three pages labeled as translucency format 108 depict translucency in a composite format. The composite formats allow other features to be included in a single image, for example, surface anatomy, characterizations crack lines, and varying translucency hues. In FIG. 8A, the images 4 are coded as follows: UT 110 for uniform translucency, COHT 112 for common incisal halo translucency, CIHT 114 for characterized incisal halo translucency, and DT 116 for defined translucency. As shown in FIG. 8A, the translucency is uniform throughout the tooth in image UT 110. The translucency is more concentrated in a region across the tooth toward the bottom, but not including the bottom edge of the tooth in images COHT 112 and CIHT 114, whereas the translucency in image DT 116 is concentrated in a region across the tooth toward the bottom including the bottom edge of the tooth. In each of these images, different surface anatomies or characterizations are simultaneously imposed on the tooth as a composite image.

In FIG. 8B, the images 4 are coded as follows: BIHT 118 for blue/incisal halo translucency, BRIHT 120 for brown incisal halo translucency, PT 122 for proximal translucency, and MT 124 for middle translucency. In addition to the surface anatomy, crack lines, and characterizations imposed on the tooth in each of the images, the translucency in images BIHT 118 and BRIHT 120 appears in a region across the bottom half of the tooth, but not including the bottom edge with the translucency taking on a blue tint in BIHT 118 and a brown tint in BRIHT 120. In image PT 122, the translucency appears on both side edges and the bottom edge of the tooth, whereas the translucency in image MT 124 appears across the middle one-third of the tooth.

In FIG. 8C, the images 4 are coded as follows: IAT 126 for incisal angles translucency, PGST 128 for progressive translucency, PDBT 130 for progressed blue translucency, and PDGT 132 for progressed gray translucency. Again, in addition to translucency characteristics, several types of surface anatomy are variously additionally imposed on the tooth to provide a reference for how a composite of such features would appear. The translucency in image IAT 126 appears concentrated toward the bottom corners of the tooth. The translucency in image PGST 128 appears more concentrated in the bottom corners of the tooth and becomes less defined toward the center of the tooth, and the images PDBT 130 and PDGT 132 show the translucency in blue and gray tints, respectively.

Figure 9A:
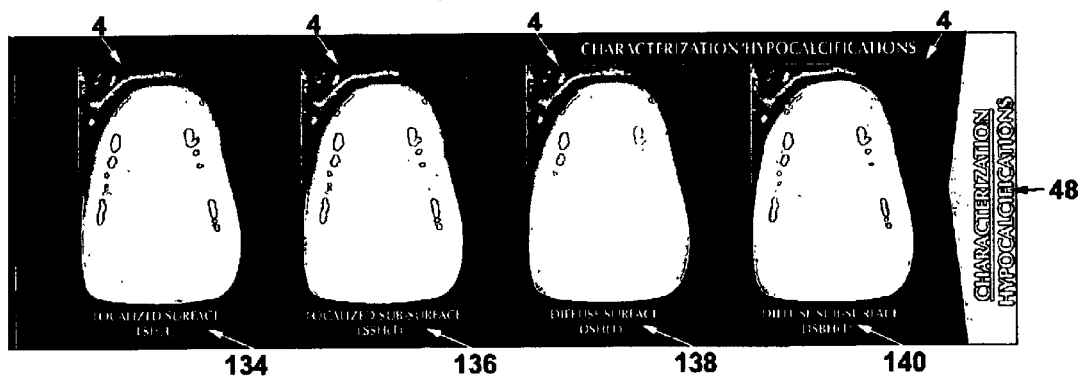
FIGS. 9A–9C are plan views of Hypocalcifications of a Characterization category pages of the booklet of FIG. 5.

Four types of hypocalcifications 48 are depicted in FIG. 9A. The images 4 may be coded as follows: LSH(T) 134 for localized surface hypocalcification, LSSH(T) 136 for localized sub-surface hypocalcification, DSH(T) 138 for diffuse surface hypocalcification, and DSBH(T) 140 for diffuse sub-surface hypocalcification. As shown in FIG. 9A, the hypocalcification is depicted in the whiter portions of the images. In images LSH(T) 134 and LSSH(T) 136, the hypocalcification is concentrated in a few locations on the tooth as opposed to being spread out over a greater portion of the tooth as in images DSH(T) 138 and DSBH(T) 140. The hypocalcification also appears closer to the surface of the tooth in images LSH(T) 134 and DSH(T) 138 as opposed to LSSH(T) 136 and DSBH(T) 140, wherein the hypocalcification appears just beneath the surface of the tooth.

Figure 9B:
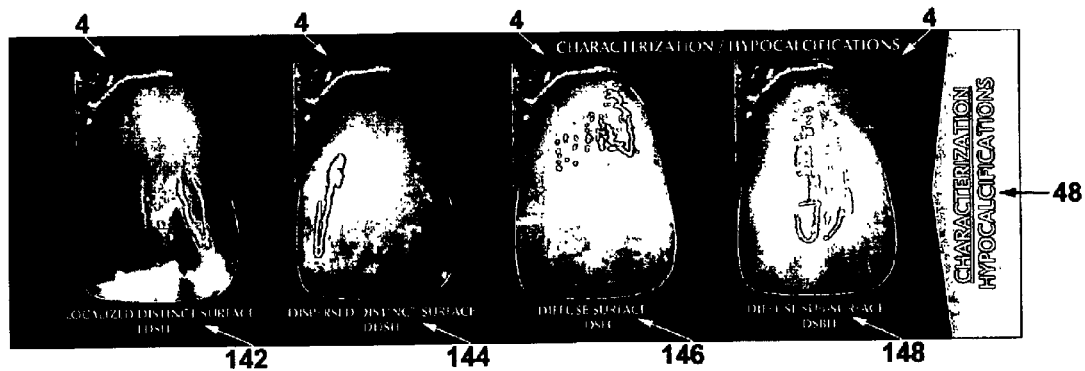
Figure 9C:
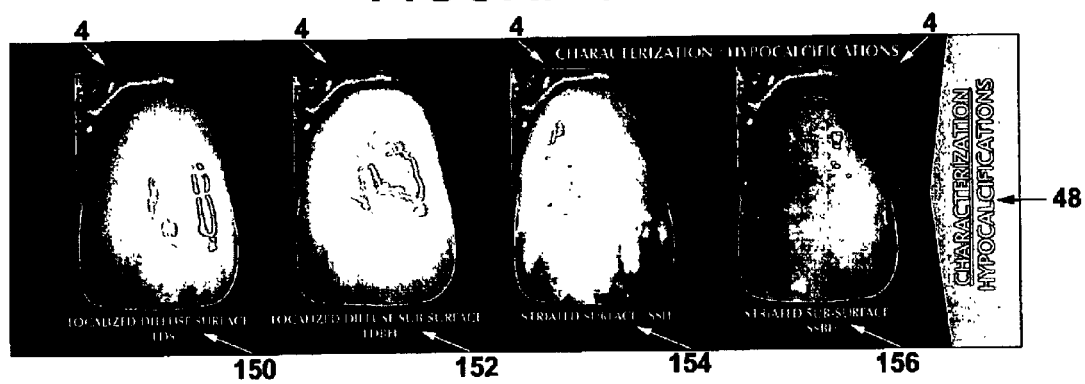

The coding for the images shown in FIG. 9A are designated with a parenthesized "T"—(T)— which designates a template image. This indicates that the individual feature is presented singularly to prevent confusion with similar coding for composite images of the same features. FIGS. 9B and 9C depict hypocalcifications 48 in composite settings using a constant template in shape and outline. In addition to the hypocalcifications 48, the composite images additionally present various combinations of, for example, surface anatomy, characterizations, chroma, and discolorations. The images 4 in FIG. 9B are coded as follows: LDSH 142 for localized distinct surface hypocalcification, DDSH 144 for dispersed distinct surface hypocalcification, DSH 146 for diffuse surface hypocalcification, and DSBH 148 for diffuse sub-surface hypocalcification. As shown in FIG. 9B, the hypocalcification in image LDSH 142 appears as defined white regions localized near the bottom edge of the tooth. The hypocalcification in image DDSH 144 appears as defined white spots that are dispersed throughout the tooth, whereas the hypocalcification in image DSH 146 appears as white areas which are less defined and appear to occur toward the surface of the tooth. The hypocalcification in image DSBH 148 appears as white areas that are less defined and appear to occur below the surface of the tooth.

In the FIG. 9C, the images are coded as follows: LDS 150 for localized diffuse surface hypocalcification, LDBH 152 for localized sub-surface hypocalcification, SSH 154 for striated surface hypocalcification, and SSBH 156 for striated sub-surface hypocalcification. As shown in FIG. 9C, the hypocalcification in image LDS 150 appears as defined white surface spots that are dispersed in a localized area toward the bottom one-third of the tooth, whereas the hypocalcifications in image LDBH 152 appear below the surface of the tooth. The hypocalcifications in SSH 154 appear in white surface spots that appear in elongated areas running from the bottom to the upper half of the tooth, whereas the hypocalcifications in image SSBH 156 appear below the surface of the tooth.

Figure 10A:
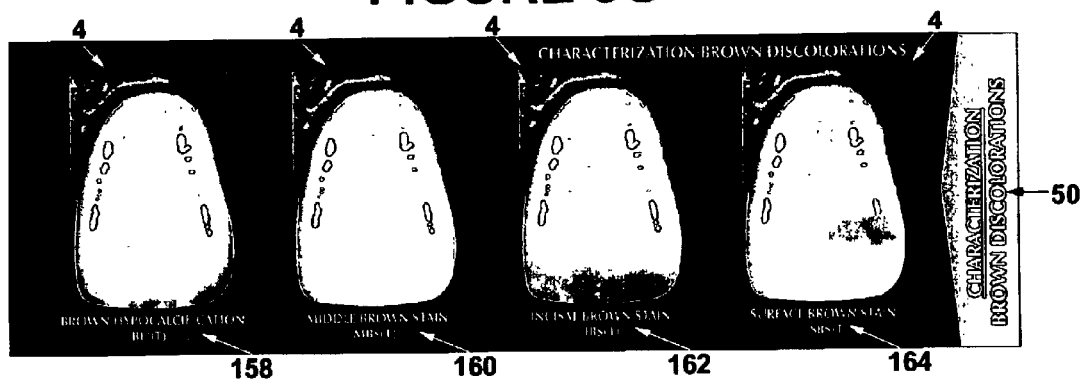
FIGS. 10A and 10B are plan views of Brown Discolorations of the Characterization category pages of the booklet of FIG. 5.

Four types of brown discolorations 50 are depicted in FIG. 10A. The images 4 may be coded as follows: BH(T) 158 for brown hypocalcification, MBS(T) 160 for middle brown stain, IBS(T) 162 for incisal brown stain, and SBS(T) 164 for surface brown stain. As shown in FIG. 10A, the brown discoloration is depicted by a brown or darker area on the tooth. For example, the brown discoloration on DH(T) 158 is depicted as a brown spot toward the center bottom of the tooth, the brown discoloration on MBS(T) 160 is depicted as a brown spot in the center of the tooth, the brown discoloration in IBS(T) 162 is depicted as a brown stain that covers most of the bottom third of the tooth, and the brown discoloration in SBS(T) 164 is depicted as a brown stain that covers most of the center third of the tooth and appears closer to the surface of the tooth. The coding for the images 4 shown in FIG. 10A are designated with a parenthesized "T"—(T)— which again designates a template image, wherein the individual feature is presented singularly to prevent confusion with similar coding for composite images including the same features.

Figure 10B:
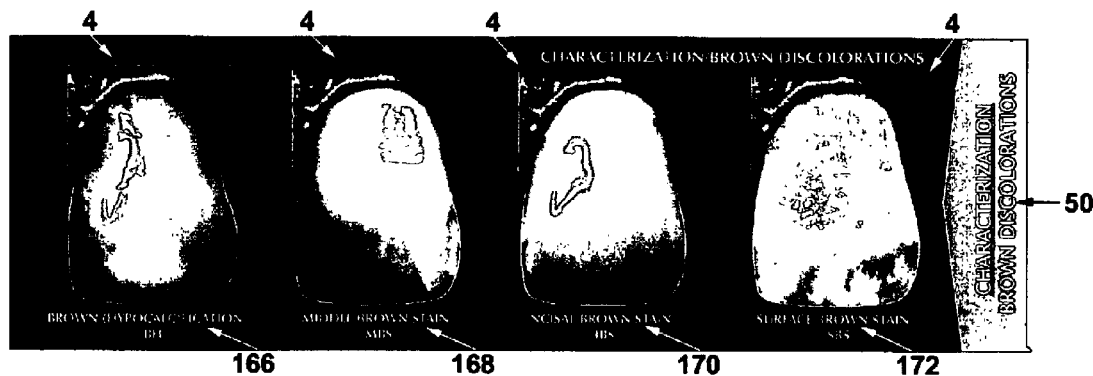

In FIG. 10B, the features shown are the same as those in FIG. 10A, but they are depicted as brown discolorations 50 in a composite setting using a constant template in shape and outline. The images 4 in FIG. 10B may be coded as follows: BH 166 for brown (hypocalcification), MBS 168 for middle brown stain, IBS 170 for incisal brown stain, and SBS 172 for surface brown stain.

Figure 11A:
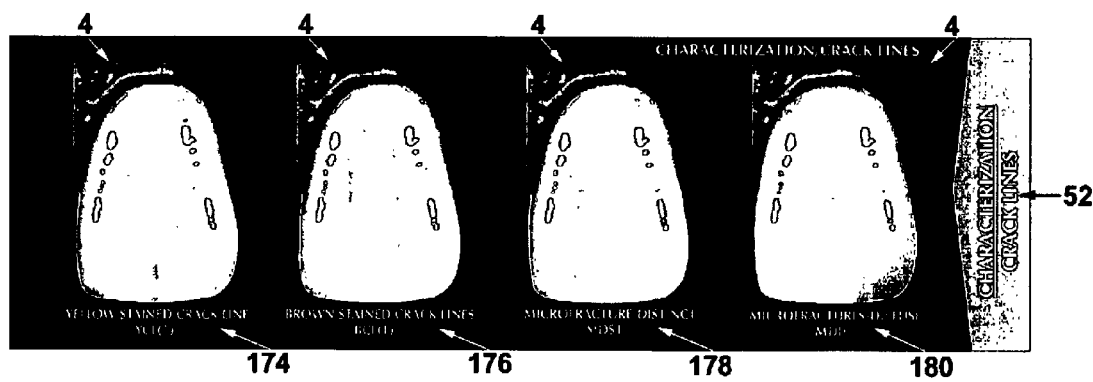
FIGS. 11A and 11B are plan views of Crack Lines of the Characterization category pages of the booklet of FIG. 5.

Four types of crack lines 52 are depicted in FIG. 11A. The images 4 may be coded as follows: YCL(T) 174 for yellow stained crack line, BCL(T) 176 brown stained crack lines, MDST 178 for microfracture—distinct, and MDIF 180 for microfractures—diffuse. As shown in FIG. 11A, image YCL(T) 174 depicts a darkened yellow crack line running from the bottom to the upper third of the center of the tooth, whereas BCL(T) 176 depicts two darkened brown crack lines running parallel from the bottom to the upper third of the tooth. The image MDST 178 depicts a small well-defined crack running from the bottom of the tooth left of center vertically to the center the tooth, whereas MDIF 180 depicts a small crack with more amorphous features running from the bottom of the tooth right of center vertically to the upper one-third of the tooth.

Figure 11B:
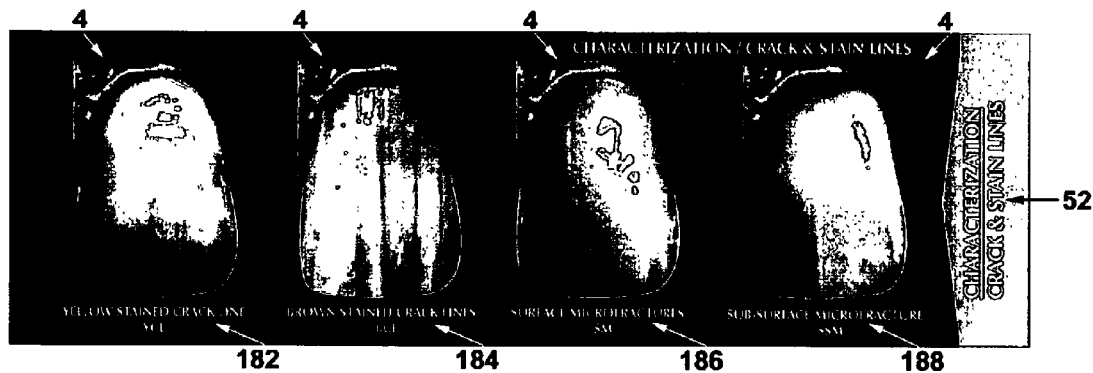

FIG. 11B depicts crack lines 52 in a composite setting using a constant template in shape and outline. The images 4 in FIG. 11B may be coded as follows: YCL 182 for yellow stained crack line, BCL 184 for brown stained crack lines, SM 186 for surface microfractures, and SSM 188 for sub-surface microfracture. The image YCL 182 depicts a single yellow-brown crack line in the center of the tooth running from the bottom to the top, whereas the image BCL 184 depicts multiple brown vertical crack lines. The image SM 186 depicts small surface crack lines (microfractures) running from the bottom of the tooth toward the top, whereas image SSM 188 depicts small crack lines (microfractures), which appear below the surface of the tooth.

Figure 12A:
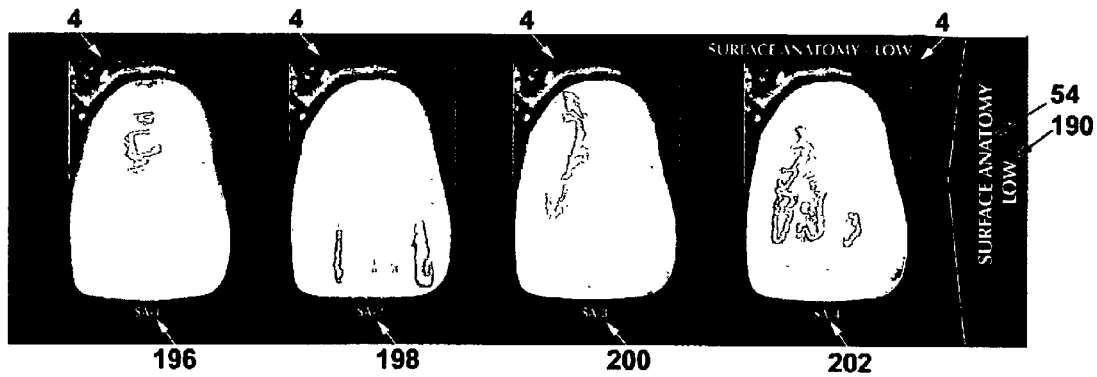
FIGS. 12A–12D are plan views of subcategories of Surface Anatomy category pages of the booklet of FIG. 5.
Figure 12B:
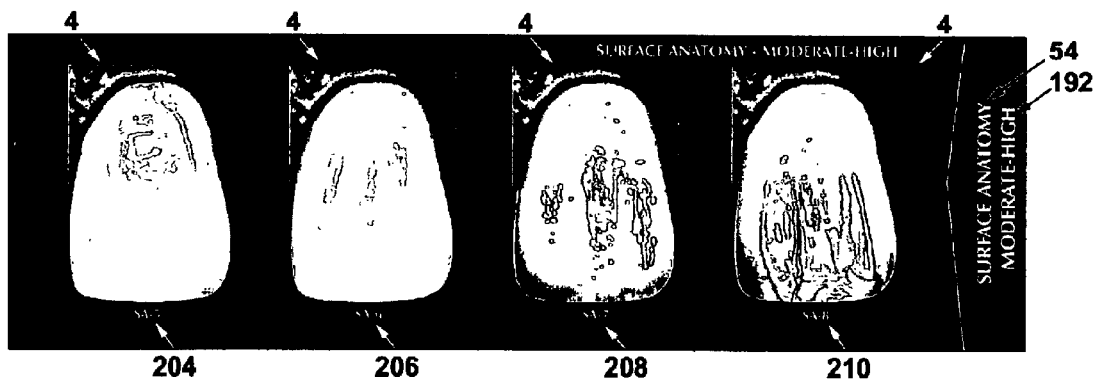

The four pages shown in FIGS. 12A–12D depict sixteen representations of surface anatomy 54. Because surface anatomy is colorless, it may be advantageous to show the images in gray scale. Surface anatomy 54 may be sub-categorized as low 190 (see FIG. 12A), moderate-high 192 (see FIG. 12B), and as having variations 194 (see FIGS. 12C and 12D). The four low surface anatomy images are coded SA-1 196, SA-2 198, SA-3 200, and SA-4 202, which correspond to increasing proportions of the surface over which the anatomy presents. The four moderate-high surface anatomy images are coded from SA-5 204, SA-6 206, SA-7 208, and SA-8 210, which correspond to even greater and increasing proportions of the surface over which the anatomy presents. Surface anatomy may be described as random bumps and indentations located in a particular area of a tooth. As shown in FIGS. 12A and 12B, the images depict an increasing surface area characterized with random bumps and indentations from SA-1 to SA-8.

Figure 12C:
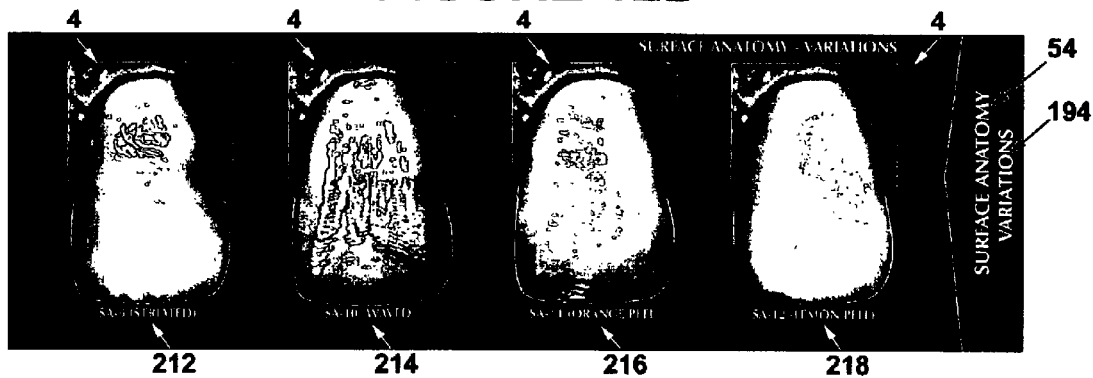
Figure 12D:
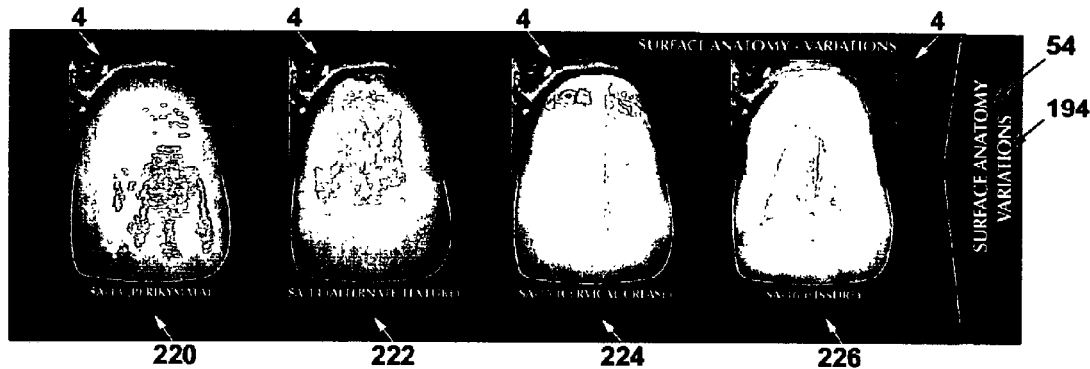

Occasionally, surface anatomy takes on a more uniform characteristic, as shown in the surface anatomy variations images of FIGS. 12C and 12D. The eight surface anatomy variations images 4 are coded as follows: SA-9 212 for striated, SA-10 214 for waved, SA-11 216 for orange peel, SA-12 218 for lemon peel, SA-13 220 for perikymata, SA-14 222 for alternate texture, SA-15 224 for cervical crease, and SA-16 226 for fissure. The image SA-9 212 depicts a tooth with a surface anatomy that resembles a striated surface. The surface anatomy in image SA-10 214 appears to have waves stacked vertically and traversing laterally across the surface of the tooth. The image SA-11 216 depicts surface anatomy that is rough over most of the surface area, with the roughness taking on the shape of the outer texture of an orange peel, whereas SA-12 218 has a less rough surface anatomy taking on the shape of the outer texture of a lemon peel. Image SA-13 220 depicts a perikymata anatomy wherein minute transverse ridges are shown on the surface of the tooth. Image SA-14 222 depicts a surface anatomy containing more than one of the previously described characteristics. Image SA-15 224 depicts a crease in the surface running vertically from top to the lower one-third of the tooth right of center, whereas image SA-16 226 depicts a fissure in the surface running from the upper one-third to the lower one-third of the tooth.

Figure 13:
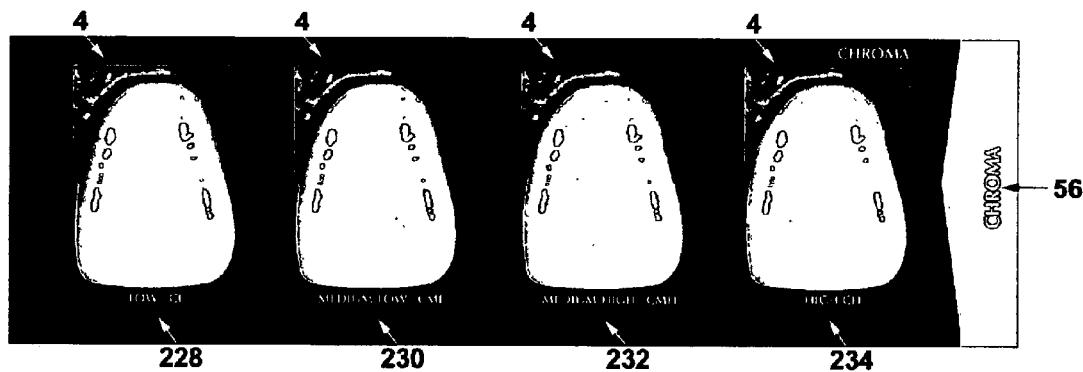
FIG. 13 is a plan view of a Chroma category page of the booklet of FIG. 5.

The category of chroma 56, or the degree of color saturation, is depicted in the four images 4 shown in FIG. 13. The chroma images may be coded as follows: CL 228 for low, CML 230 for medium-low, CMH 232 for medium-high, and CH 234 for high. As shown in FIG. 13, the images become progressively more yellow in color from CL 228 to CH 234.

Figure 14:
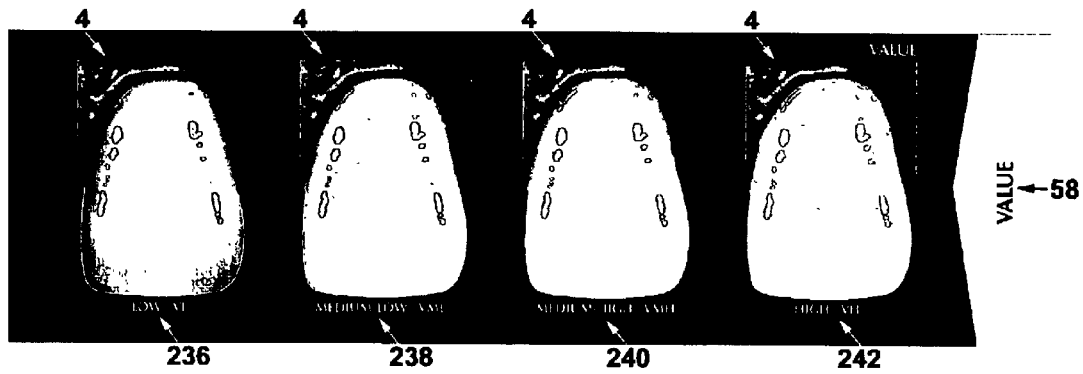
FIG. 14 is a plan view of a Value category page of the booklet of FIG. 5.

The category of value 58, or the degree of brightness, is depicted in the four images 4 shown in FIG. 14. The value images 4 may be coded as follows: VL 236 for low, VML 238 for medium-low, VMH 240 for medium-high, and VH 242 for high. As shown in FIG. 14, the images become progressively brighter from VL 236 to VH 242.

Figure 15:
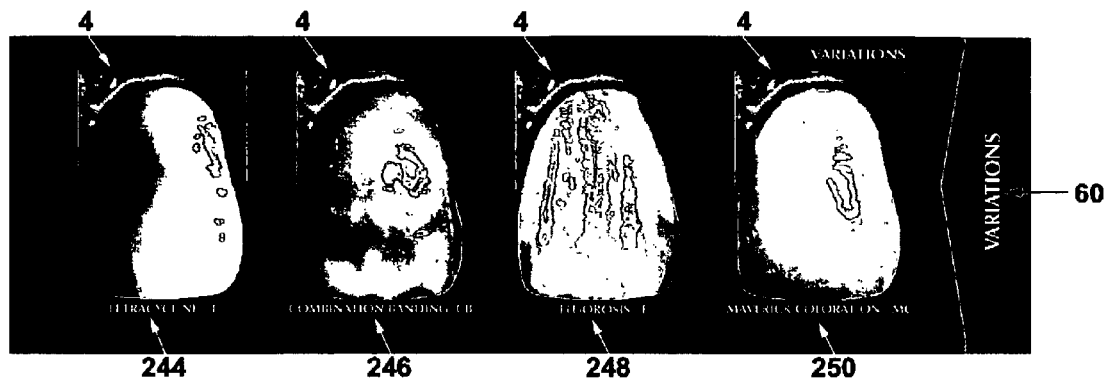
FIG. 15 is a plan view of a Variations category page of the booklet of FIG. 5.

The category of variations 60, which combines features in less commonly occurring formats, is depicted in the four images 4 shown in FIG. 15. The variations images 4 may be coded as follows: T 244 for tetracycline, CB 246 for combination banding, F 248 for fluorosis, and MC 250 for maverick coloration. As shown in FIG. 15, the image T 244 shows a tooth with a blue/green color in the lower half and the upper one-fourth of the tooth, but with a darker region between. The image CB 246 shows a tooth with color bands reaching laterally across the tooth. The image F 248 shows areas of the tooth that are especially bright. The image MC 250 shows various colors dispersed throughout the tooth.

The LADDER may also be used to supplement standardized methods known in the dental industry for choosing a base color or shade 30 (see FIG. 3) in a tooth restoration. For instance, Vita® porcelain, which is commonly known in the dental industry, is available in four different categories of base shades 30 labeled as A, B, C, and D. In addition, Vita® porcelain is available in five different hues within the A category, four different hues within the B category, four different hues within the C category, and three different hues within the D category. The images in the LADDER may be presented in combination with the various shades 30 of Vita® porcelain, or any other standardized color scheme, as a supplement to the standard LADDER schema to indicate how a finished restoration on a particular type of porcelain or ceramic might appear.

Figure 16A:
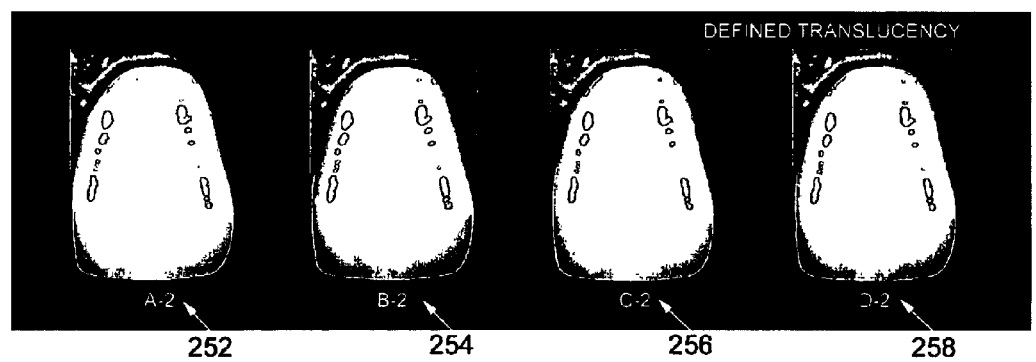
FIGS. 16A–16D are plan views of selected images from the booklet of FIG. 5 superimposed on different shades of Vita® porcelain.
Figure 16B:
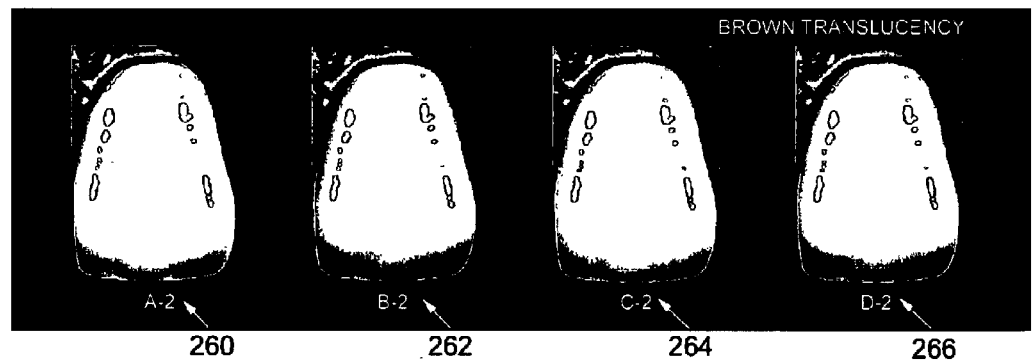
Figure 16C:
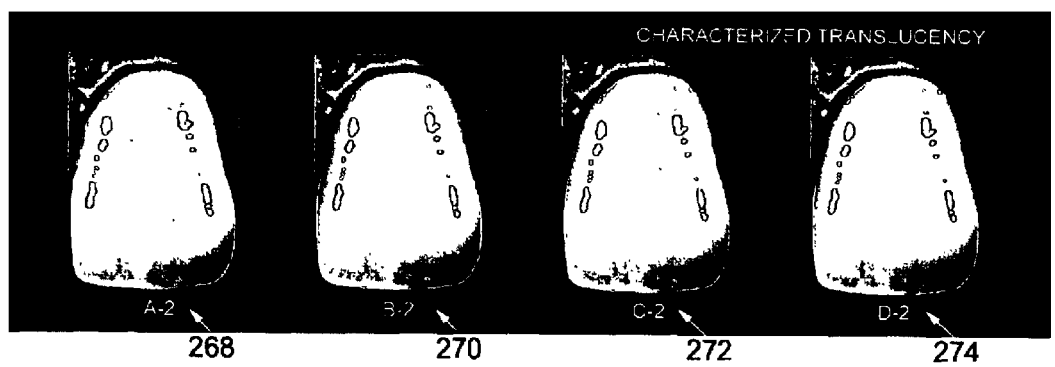
Figure 16D:
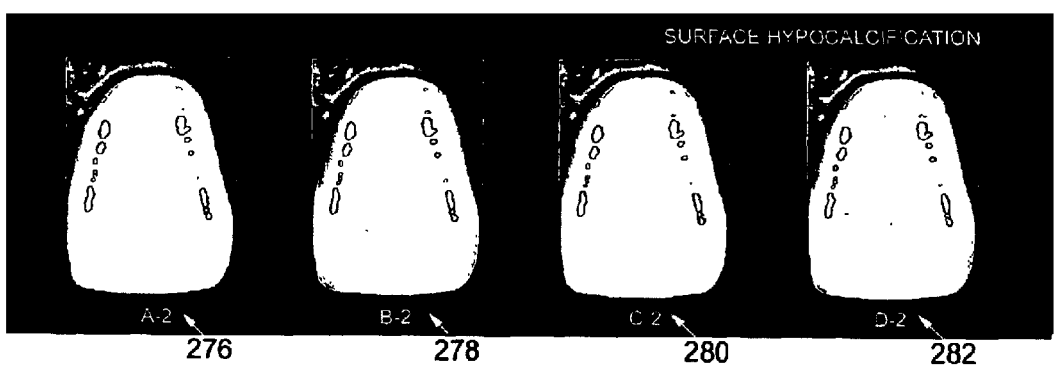

For example, FIG. 16A depicts four images of a tooth coded as defined translucency (DIT-L 74 in FIG. 6A) from the LADDER displayed in Vita® porcelain shades A-2 252, B-2 254, C-2 256, and D-2 258. Four images of a tooth coded as brown translucency (BIT-L 80 in FIG. 6B) from the LADDER are similarly displayed in Vita® porcelain shades A-2 260, B-2 262, C-2 264, and D-2 266, as depicted in FIG. 16B. FIG. 16C depicts four images of a tooth coded as characterized translucency (CIT-L 86 in FIG. 6C) from the LADDER displayed in Vita® porcelain shades A-2 268, B-2 270, C-2 272, and D-2 274. Four images of a tooth coded as diffuse surface hypocalcification (DSH (T) 138 in FIG. 9A) from the LADDER are similarly displayed in Vita® porcelain shades A-2 276, B-2 278, C-2 280, and D-2 282, as depicted in FIG. 16D. The Vita® porcelain shades are mentioned here to demonstrate by example how the LADDER may be used to supplement any standardized restoration material coloring scheme, and it is not limited to use with the Vita® porcelain shades shown. Images of the types described in FIGS. 16A–16D may be displayed on a sheet rather than booklet form or in smaller sizes in order to accommodate additional feature variations or include each of the hues in each shade category.

Figure 3A:
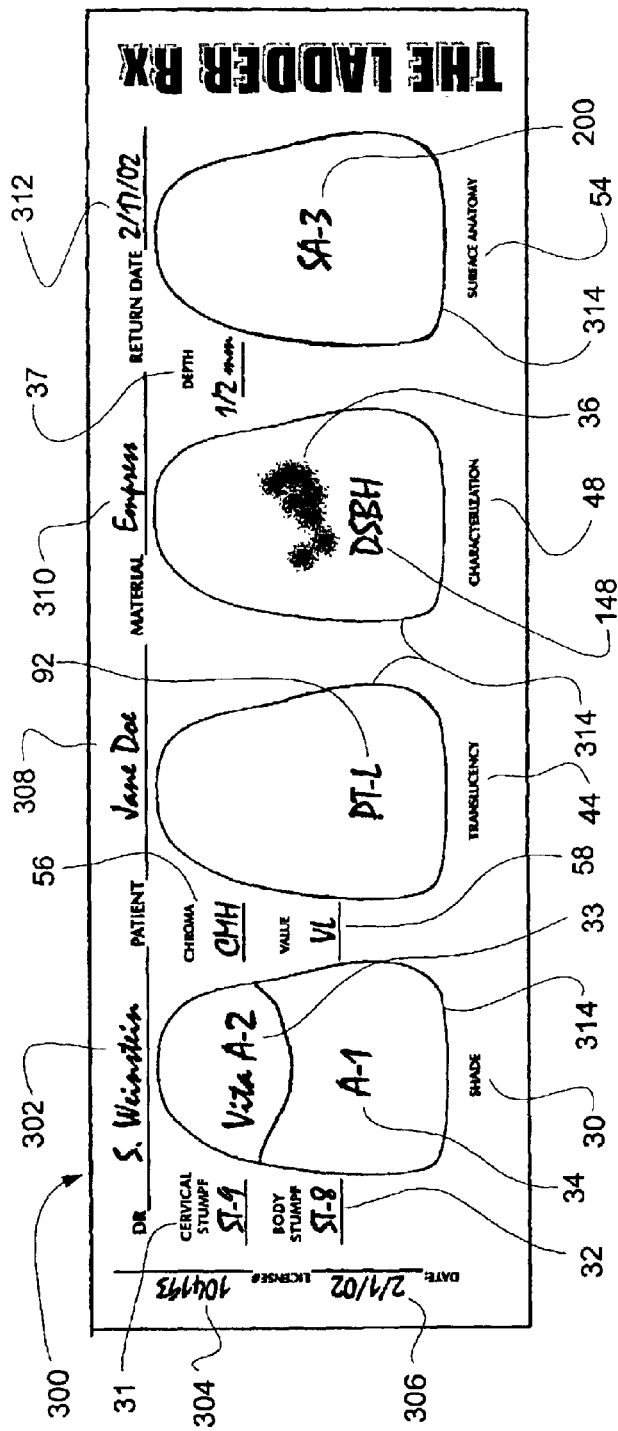
FIG. 3 is a plan view of a diagnosis form for use with a communication tool of the present invention in a booklet form.

With this understanding of the LADDER scheme, the prescription form 300 of FIG. 3 may now be described in further detail. In addition to the dentist and patient identification information described above, several fields are provided on the prescription form 300 to communicate the information necessary to recreate an accurate tooth appearance in a restoration. It should be understood that although the schematic tooth template 314 shown in FIG. 3A (as well as in FIGS. 3B–3D) is in the form of a right maxillary incisor, the prescription form 300 could depict any tooth form, e.g., canines and molars. Further, the schematic tooth templates 314 are merely meant to be used as shorthand for identifying the locations of certain tooth characteristics on the tooth to be restored. Casts of the natural dentition or other common methodologies are used to indicate the actual shape of the tooth to be restored.

Several factors may be considered in determining the base shade of the tooth restoration. Initially, the principal shade 30 of the tooth restoration must be chosen to match the natural dentition. This may be done by indicating one or more shades 30 on the tooth template 314. For example, in prescription 300 of FIG. 3, the upper or cervical portion of the tooth shape 314 is indicated as Vita® shade A-2 33, whereas the body portion is indicated as A-1 34. These shades may be determined by comparing the natural dentition to a Vita® shade guide, for example, as depicted in FIGS. 16A–D, or by comparison to any other industry shade guide. Since the color of the underlying dentin preparations may greatly effect the color of ceramic restorations, the prescription form 300 includes fields for recording, for example, the cervical Stumpf shade 31 and the body Stumpf shade (Stumpf Shade Guide, Ivoclar, Amherst, N.Y.). The shade 30 is also affected by the chroma 56 and the value 58. On the exemplary prescription form 300, values of CMH 232 for chroma 56 and VL 236 for value 58 from FIGS. 13 and 14 on the LADDER 2 are entered in the appropriate fields.

The prescription form 300 provides additional tooth templates 314 for the recordation of specific characteristics of the other categories 42 of tooth appearance classified in the LADDER 2. It should be recognized that one or more characteristics of tooth appearance in each category 42 may be present in a subject tooth and each of these characteristics is then combined to create an appropriate restoration. The second tooth template 314 is designated to receive information regarding the translucency category 44. In the exemplary prescription form 300 of FIG. 3, the PT-L 92 code of FIG. 6D for proximal translucency-low is indicated. The third tooth template 314 on the exemplary prescription form 300 is provided to record an indication of characterization 62. In FIG. 3, the characterization recorded is DSBH 148, or diffuse sub-surface hypocalcification, as depicted in FIG. 9B on the LADDER 2. The tooth template of prescription form also allows the dentist to indicate the area 36 of the tooth upon which the characteristic of tooth appearance should appear on the restoration. The final tooth template 314 on the prescription form 300 is for the recordation of surface anatomy 54, which in this exemplary case is indicated as SA-3, as shown in FIG. 12A on the LADDER 2. An additional field of depth 37 is provided to allow the dentist to indicate the depth of the features of the surface anatomy 54 in the surface of the tooth.

Once a ceramist receives a prescription form, he must then determine how to recreate the indicated characteristics into the desired tooth appearance in a restoration. This typically requires great knowledge and skill on the part of the ceramist in choosing, for example, the appropriate ceramic or porcelain, the colors and surface treatments, and whether cutbacks or multiple bake cycles are required to achieve the desired effects. Unfortunately, in the hands of a less skilled ceramist, even the best instructions may not result in a quality restoration. This disparity in quality of restorations may be alleviated, however, by providing recipes corresponding to each of the tooth characteristics depicted in the ladder.

The LADDER may incorporate multiple formulations for each applicable image outlining the necessary tints, opaquers, and mixtures respective to dominant porcelain/ceramic manufacturers. The colors, modifiers, and other applications are essentially the same to achieve the image, but termed differently by each manufacturer. For example, Jeneric-Pentron (Wallingford, Conn.) manufactures Finesse® porcelain and Vita manufactures Vita® porcelain. For example, one might take samples of an incisal modifier from both manufacturers and find them to be identical in coloration, while Jeneric-Pentron labels this modifier "blue incisal" and Vita labels this modifier as "indigo incisal."

Most all dental laboratories tend to use one or two lines of porcelain or ceramic. The set-up expense of having multiple lines is quite costly. Outlining multiple "recipes" using the jargon of varied manufacturers thus accommodates universal applicability of the reference. The recipes themselves readily allow for an average technician to output a much higher quality of esthetic restoration and encourages such by eliminating the time and costs of experimentation to achieve the desired effects.

Several exemplary recipes are shown in FIGS. 3B–3D. FIG. 3B depicts a restoration recipe 350 for the LSSH(T) 136 image, or localized sub-surface hypocalcification characteristic, of FIG. 9A on the LADDER 2 as prepared on Finess® Low-Fusing Ceramic. The base shade 352 of the majority of the restoration is Vita® A-1. Portions of the upper tooth 354 are shaded in Vita® A-2, as indicated. Also the upper portion of the tooth restoration 356 is coated with a natural light incisal enamel overlay, as indicated. The middle to lower body of the tooth 358 is coated with a layer of A-1 Dentin mixed with Clear in a 50/50 ratio. A non-mamelon cutback 366 is indicated between the middle and lower third of the tooth. A discoloration or stain 360 is indicated and is created using Faint White. In the center of the bottom third of the tooth, an area 362 of different coloration is indicated and is created using Ivory Opal. Finally, the tip of the tooth 364 is tinted using A-1 and Clear Halo in a 75/25 mixture, respectively. The colors and treatments used in creating this tooth restoration are all standard colors and treatments used as part of the Finesse® restoration system.

FIG. 3C depicts a second restoration recipe 350 for creating a restoration shown in the CIT-M 88 image, characterized incisal translucency-medium characteristic of FIG. 6C. This recipe is again based upon a tooth restoration material of Finesse® Low-Fusing Ceramic. In this exemplary recipe, the base shade 368 of the restoration is again Vita® A-1. Portions of the upper half of the restoration 370 are again Vita® A-2 shade, as indicated. Additional areas of the upper half of the restoration 372 are overlayed with Natural White Incisal Enamel, as indicated. Three mamelon cutbacks 378 are indicated in the lower third of the restoration and are tinted to match the Vita® B-1 shade. Below the mamelon cutbacks 378 is an area to be covered with Natural Light Enamel Incisal. Finally, the tip of the tooth restoration 380 is colored using A-1 Dentin Halo.

FIG. 3D depicts a third exemplary restoration recipe 350, this time using a base material of Ducera® porcelain. The colors and treatments in this recipe, therefore, are specific to a Ducera® restoration system. The tooth appearance to be created by the restoration is MBS 160, or middle brown stain, as depicted in FIG. 10A. The base shade 382 of this restoration is Vita® A-3. The top of the tooth adjacent to gingival tissue 386 is then shaded to match Vita® A-3. The bottom two thirds 382 of the tooth are also covered by a layer of Natural White mixed with Blue Opal in a 50/50 ratio. An area of the middle third of the tooth 388 is tinted using White Opal Incisal. Additionally, the central area between the middle third and bottom third of the tooth 385 indicates that a mamelon colored Amber should be built up in this area. Vertical crack lines 384 tinted in White are also indicated at several locations on the tooth. Finally, several areas at the bottom tip of the tooth 387 are colored White Opal, as indicated.

FIG. 3E depicts a third exemplary restoration recipe 350, this time using a base material of Vita® porcelain. The colors and treatments in this recipe, therefore, are specific to a Vita® restoration system. The tooth appearance to be created by the restoration is PDBT 130, or progressed blue translucency, as depicted in FIG. 8C. The base shade 396 of this restoration is Vita® D-3. The top of the tooth adjacent to gingival tissue 390 and extending down the sides is then tinted with a mixture of Vita® D-3 Dentin and Coral in a 90/10 ratio, respectively, to build a mamelon area. The bottom quarter of the restoration and extending up the sides to partially overlap the area of D-3 Dentin and Coral 392 is tinted with a mixture of two parts Natural Medium Incisal and three parts Blue Opal. Finally, a portion of the bottom tip of the tooth 394 is colored with White Opal.

Although the description of the invention has thus far focused on the use of a booklet containing images depicting various features of tooth appearance in order to document and communicate these features to the laboratory technician or ceramist, a dentist or dental auxiliary may use various other means for displaying images. For example, images may be stored on a computer server for ready access by a user. Composite images may also be displayed by using semi-transparent overlays or computer morphing software. The dentist could then select the appropriate image presented on the visual display and a software program could automatically record the selection for preparation of a prescription. Computers linked via a communication network, for example, a local area network or the Internet, could further enable a user to transmit a prescription directly to the laboratory. When displaying images using a monitor or overlays, care must be exercised to insure that the quality and consistency of the images are not diminished.

Figure 17:
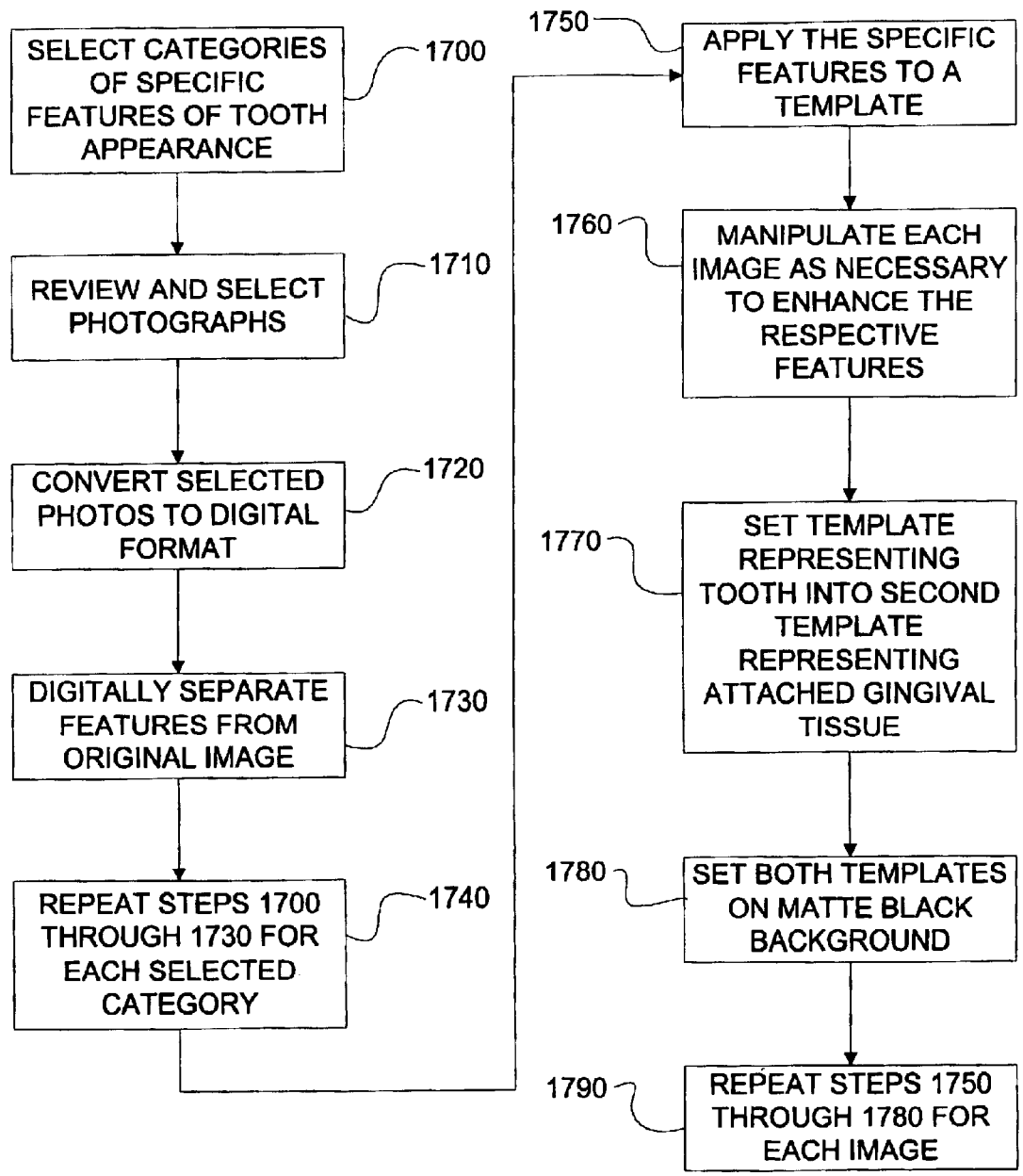
FIG. 17 is a flow diagram of a method to create images of dental characteristics for a communication tool according to the present invention.

The quality and type of images viewed by users of the LADDER are an important aspect of the invention, because they help to assure more accurate communication of specific features of tooth appearance between the dentist or dental auxiliary and the laboratory technician or ceramist. In one embodiment of the invention, the images may be created according to the method depicted in FIG. 17. In step 1700, various categories of specific features of appearance for a particular type of tooth are selected. Representative photographs taken of specific teeth are reviewed and certain ones of the photographs are selected in step 1710. The selected photographs are then, in step 1720, converted to a digital format. Although step 1720 calls for the photographs to be converted to a digital format, other means may also be utilized, such as photo manipulation, separation, and filtering. Specific features are then digitally or photographically separated from the original image in step 1730. Steps 1700 through 1730 are then, in step 1740, repeated for each selected category. The specific features are then applied to a respective template in step 1750. Any necessary further manipulation of each image that may be required to heighten or enhance the respective feature is carried out in step 1760. The template representing the tooth is then, in step 1770, set into a second template representing attached gingival tissue. Both templates are then, in step 1780, set on a matte black background for contrast. Steps 1750 through 1780 are then repeated for each image (step 1790). Because the various features depicted on the images have been enhanced, less subjectivity and expertise is involved with selecting an image that accurately reflects the specific feature of a patient's tooth. Although the images have been manipulated, they are true representations of natural phenomenon.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A method of making a communication tool for communicating characteristics of observable tooth appearance comprising:

designating a category of tooth appearance, wherein the category comprises at least one specific feature of tooth appearance;

selecting a particular specific feature;

reviewing a plurality of images of teeth;

selecting one of the images of a particular tooth, wherein the particular tooth represents the particular specific feature;

separating the particular specific feature from the selected image;

applying the separated particular specific feature to an image of an exemplary tooth to create an exemplary specific feature image;

assigning a code to uniquely identify the exemplary specific feature image; and displaying the exemplary specific feature image and the assigned code in combination on a means perceivable to a user.

2. The method of claim 1, further comprising providing a means for documenting the assigned code when an actual feature similar to the exemplary specific feature image is observed in a subject tooth by a user of the communication tool.

3. The method of claim 1, further comprising providing a recipe related to the assigned code, the recipe providing instructions for recreating the particular specific feature identified by the assigned code; and wherein the step of displaying further comprises displaying the recipe on the means perceivable to the user.

4. A method of making a communication tool for communicating characteristics of observable tooth appearance comprising:

selecting a particular specific feature of tooth appearance;

reviewing a plurality of images of teeth;

selecting one of the images of a particular tooth, wherein the particular tooth represents the particular specific feature;

separating the particular specific feature from the selected image; and applying the separated particular specific feature to an image of an exemplary tooth to create an exemplary specific feature image.

5. The method of claim 4, further comprising displaying the exemplary specific feature image on a means perceivable to a user.

* * * * *